US011779547B2

(12) United States Patent
Shah et al.

(10) Patent No.: US 11,779,547 B2
(45) Date of Patent: Oct. 10, 2023

(54) MULTIPARTICULATE L-MENTHOL FORMULATIONS AND RELATED METHODS

(71) Applicant: Société des Produits Nestlé S.A., Vevey (CH)

(72) Inventors: Syed M. Shah, Boca Raton, FL (US); Daniel Hassan, Boca Raton, FL (US)

(73) Assignee: Société des Produits Nestlé S.A., Vevey (CH)

( * ) Notice: Subject to any disclaimer, the term of this patent is extended or adjusted under 35 U.S.C. 154(b) by 0 days.

(21) Appl. No.: 14/853,458

(22) Filed: Sep. 14, 2015

(65) Prior Publication Data

US 2016/0000728 A1    Jan. 7, 2016

Related U.S. Application Data

(63) Continuation of application No. 14/064,685, filed on Oct. 28, 2013, now Pat. No. 9,132,095, which is a continuation of application No. 13/367,747, filed on Feb. 7, 2012, now Pat. No. 8,568,776.

(60) Provisional application No. 61/486,523, filed on May 16, 2011, provisional application No. 61/441,716, filed on Feb. 11, 2011.

(51) Int. Cl.
*A61K 9/50* (2006.01)
*A61K 31/045* (2006.01)
*A61K 9/00* (2006.01)

(52) U.S. Cl.
CPC .......... *A61K 31/045* (2013.01); *A61K 9/0053* (2013.01); *A61K 9/50* (2013.01); *A61K 9/5026* (2013.01); *A61K 9/5042* (2013.01); *A61K 9/5047* (2013.01); *A61K 9/5073* (2013.01); *A61K 9/5089* (2013.01)

(58) Field of Classification Search
CPC ...... A61K 31/045; A61K 9/0053; A61K 9/50; A61K 9/5026; A61K 9/5042; A61K 9/5047; A61K 9/5073; A61K 9/5089; A61K 47/38; A61P 1/00; A61P 1/04
See application file for complete search history.

(56) References Cited

U.S. PATENT DOCUMENTS

| | | | |
|---|---|---|---|
| 1,811,777 A | 6/1931 | Blagden | |
| 2,366,749 A * | 1/1945 | Ofner | C07C 35/12 568/829 |
| 3,515,781 A | 6/1970 | Steinberg | |
| 4,687,667 A | 8/1987 | Rhodes et al. | |
| 4,786,505 A | 11/1988 | Lovgren et al. | |
| 4,808,413 A * | 2/1989 | Joshi | A61K 9/1617 424/458 |
| 4,867,985 A * | 9/1989 | Heafield | A61K 9/1652 424/458 |
| 5,328,682 A * | 7/1994 | Pullen | A61K 8/044 424/49 |
| 5,362,745 A | 11/1994 | Graziella | |
| 5,397,573 A * | 3/1995 | Kajs | A61K 9/4891 424/451 |
| 5,418,010 A | 5/1995 | Janda et al. | |
| 5,498,423 A | 3/1996 | Zisapel | |
| 5,688,510 A * | 11/1997 | Nakamichi | A61K 9/1694 424/43 |
| 5,840,332 A | 11/1998 | Lerner et al. | |
| 6,139,877 A | 10/2000 | Debregeas et al. | |
| 6,306,435 B1 | 10/2001 | Chen et al. | |
| 6,365,185 B1 | 4/2002 | Ritschel et al. | |
| 6,423,349 B1 | 7/2002 | Sherratt et al. | |
| 6,531,152 B1 | 3/2003 | Lerner et al. | |
| 6,632,451 B2 | 10/2003 | Penhasi et al. | |
| 6,726,927 B2 | 4/2004 | Chen | |
| 6,972,132 B1 | 12/2005 | Kudo et al. | |
| 7,041,316 B2 | 5/2006 | Chen | |
| 7,048,945 B2 | 5/2006 | Percel et al. | |
| 7,115,282 B2 | 10/2006 | Shefer et al. | |
| 7,670,619 B2 | 3/2010 | Mihaylov | |
| 7,670,624 B2 | 3/2010 | Tsutsumi et al. | |
| 7,790,215 B2 | 9/2010 | Sackler et al. | |
| 7,790,755 B2 | 9/2010 | Akiyama et al. | |
| 7,803,817 B2 | 9/2010 | Kostadinov et al. | |
| 7,829,122 B2 | 11/2010 | Bruna et al. | |
| 7,838,027 B2 | 11/2010 | Rao et al. | |
| 8,337,811 B1 | 12/2012 | Sung et al. | |
| 8,361,439 B1 | 1/2013 | Sung et al. | |
| 8,524,257 B2 | 9/2013 | Nowak et al. | |
| 8,535,640 B1 | 9/2013 | Sung et al. | |

(Continued)

FOREIGN PATENT DOCUMENTS

| | | | |
|---|---|---|---|
| CN | 101596166 A | * | 12/2009 |
| CN | 1886119 B | | 4/2015 |

(Continued)

OTHER PUBLICATIONS

Office Action for U.S. Appl. No. 14/918,042 dated May 11, 2016.
Hawthorne, M; The Actions of Peppermint Oil and Menthol on Calcium Channel Dependent Processes in Intestinal, Neuronal and Cardiac Preparations; Department of Biochemical Pharmacology, State University of New York; Oct. 14, 1987.
Office Action for U.S. Appl. No. 14/524,648 dated Mar. 24, 2016.
Office Action for U.S. Appl. No. 14/876,465 dated Jan. 25, 2016.
Office Action for U.S. Appl. No. 14/918,042 dated Jan. 8, 2016.

(Continued)

*Primary Examiner* — Ali Soroush
(74) *Attorney, Agent, or Firm* — Christopher M. Ramsey; GrayRobinson, P.A.

(57) ABSTRACT

An L-menthol pharmaceutical dosage form includes an effective amount of L-menthol for treating a gastrointestinal disorder. The L-menthol is within a plurality of particulates having a core and an enteric coating over the core. The core includes an L-menthol source that is at least 80% pure L-menthol. The dosage form may be used to treat gastrointestinal disorders, such as irritable bowel syndrome.

16 Claims, 1 Drawing Sheet

(56) References Cited

U.S. PATENT DOCUMENTS

| | | | |
|---|---|---|---|
| 8,545,880 B2 | 10/2013 | Li et al. | |
| 8,568,776 B2 | 10/2013 | Shah et al. | |
| 8,574,544 B1 | 11/2013 | Sung et al. | |
| 8,808,736 B2 | 8/2014 | Shah et al. | |
| 2001/0038863 A1 | 11/2001 | Jaenicke et al. | |
| 2002/0114832 A1 | 8/2002 | Herrmann et al. | |
| 2002/0192285 A1 | 12/2002 | Mulye | |
| 2002/0192885 A1 | 12/2002 | Miyasaka | |
| 2003/0040539 A1 | 2/2003 | Zisapel | |
| 2003/0064106 A1 | 4/2003 | Garces et al. | |
| 2003/0143272 A1 | 7/2003 | Waterman | |
| 2003/0198673 A1* | 10/2003 | Oshlack | A61K 9/2846 424/468 |
| 2003/0207851 A1 | 11/2003 | Wei | |
| 2004/0052846 A1 | 3/2004 | Prater et al. | |
| 2004/0062778 A1 | 4/2004 | Shefer et al. | |
| 2004/0191402 A1 | 9/2004 | Stawski et al. | |
| 2005/0069579 A1 | 3/2005 | Kamaguchi et al. | |
| 2005/0129761 A1 | 6/2005 | Venkata Ramana Rao et al. | |
| 2005/0164987 A1 | 7/2005 | Barberich | |
| 2005/0169987 A1 | 8/2005 | Korber | |
| 2005/0181047 A1 | 8/2005 | Romero | |
| 2005/0202079 A1 | 9/2005 | Bielski et al. | |
| 2005/0281876 A1 | 12/2005 | Li et al. | |
| 2006/0009465 A1 | 1/2006 | Edgar et al. | |
| 2006/0039872 A1* | 2/2006 | Schmidt | A23G 4/043 424/48 |
| 2006/0165794 A1* | 7/2006 | Chenevier | A61K 9/2081 424/472 |
| 2006/0210631 A1 | 9/2006 | Patel et al. | |
| 2006/0217489 A1 | 9/2006 | Yako et al. | |
| 2006/0246134 A1 | 11/2006 | Venkatesh | |
| 2006/0257469 A1 | 11/2006 | Bulka | |
| 2006/0280795 A1 | 12/2006 | Penhasi et al. | |
| 2007/0231388 A1 | 10/2007 | Anstett-Klein et al. | |
| 2007/0292510 A1 | 12/2007 | Huang | |
| 2008/0139510 A1 | 6/2008 | Rose | |
| 2008/0152719 A1 | 6/2008 | Petereit et al. | |
| 2008/0166416 A1 | 7/2008 | Lizio et al. | |
| 2008/0199518 A1 | 8/2008 | Ku et al. | |
| 2008/0299199 A1 | 12/2008 | Bar-Shalom et al. | |
| 2009/0004262 A1 | 1/2009 | Shaw et al. | |
| 2009/0004281 A1 | 1/2009 | Nghiem et al. | |
| 2009/0137670 A1 | 5/2009 | Kramer et al. | |
| 2009/0227670 A1 | 9/2009 | Berg | |
| 2009/0238905 A1 | 9/2009 | Gurney et al. | |
| 2009/0246301 A1 | 10/2009 | Ehrenpreis et al. | |
| 2010/0119601 A1 | 5/2010 | McCarty | |
| 2010/0183713 A1 | 7/2010 | Tsutsumi et al. | |
| 2010/0203134 A1 | 8/2010 | Chenevier et al. | |
| 2010/0297251 A1* | 11/2010 | Timmons | A61K 9/5015 424/501 |
| 2010/0298379 A1 | 11/2010 | Jacobsen | |
| 2011/0053866 A1 | 3/2011 | Duffield et al. | |
| 2011/0064830 A1 | 3/2011 | Piotrowski | |
| 2011/0081451 A1 | 4/2011 | Siegel et al. | |
| 2011/0092605 A1 | 4/2011 | Yan | |
| 2012/0207842 A1 | 8/2012 | Shah et al. | |
| 2012/0277323 A1 | 11/2012 | Kumar et al. | |
| 2012/0301541 A1 | 11/2012 | Haronsky et al. | |
| 2012/0301546 A1 | 11/2012 | Hassan | |
| 2013/0230597 A1 | 9/2013 | Cook et al. | |
| 2014/0178468 A1 | 6/2014 | Shear et al. | |

FOREIGN PATENT DOCUMENTS

| | | | |
|---|---|---|---|
| EP | 0015334 B1 | 5/1982 | |
| EP | 1953625 A | 8/2008 | |
| EP | 1958625 A1 | 8/2008 | |
| JP | 53039503 | 10/1978 | |
| JP | 62226926 | 10/1987 | |
| JP | 2000247870 | 9/2000 | |
| JP | 2007197378 | 8/2007 | |
| JP | 2008127349 | 6/2008 | |
| JP | 2010189443 | 9/2010 | |
| JP | 5201819 | 6/2013 | |
| JP | 2015024986 | 2/2015 | |
| KR | 20060118452 A | 11/2006 | |
| WO | WO-9428895 A2 * | 12/1994 | A61K 31/045 |
| WO | 9513794 | 5/1995 | |
| WO | 9959544 | 11/1999 | |
| WO | WO-0230398 A2 * | 4/2002 | A61K 9/1652 |
| WO | 2005027878 A1 | 3/2005 | |
| WO | 2005032513 A2 | 4/2005 | |
| WO | 2006097427 A1 | 9/2006 | |
| WO | 2007012856 A | 2/2007 | |
| WO | 2008057802 A | 5/2008 | |
| WO | 2008134807 A1 | 11/2008 | |
| WO | 2009077749 A | 6/2009 | |
| WO | 2010144943 A1 | 12/2010 | |
| WO | 2011111027 A2 | 9/2011 | |
| WO | 2012109216 A | 8/2012 | |
| WO | 2012170488 A | 12/2012 | |
| WO | 2012170611 A | 12/2012 | |
| WO | 2014065390 A1 | 5/2014 | |

OTHER PUBLICATIONS

Tran et al., New findings on melatonin absorption and alterations by pharmaceutical excipients using the Ussing chamber technique with mounted rat gastrointestinal segments, International Journal of Pharmaceuticals 378 (2009) pp. 9-16, Bioavailability Control Laboratory, College Pharmacy, Kangwon National University, Chuncheon 200-701, Republic of Korea.

Trimble et al., Heightened Visceral Sensation in Functional Gastrointestinal Disease is not site-specific, Digestive Diseases and Sciences, vol. 40, No. 8, Aug. 1995, pp. 1607-1613.

White et al., A pharmacokinetic comparison of two delayed-release peppermint oil preparations, Colpermin and Mintec, for treatment of the irritable bowel syndrome, International Journal of Pharmaceutics, vol. 40, 1987, pp. 151-155, Ipswich, United Kingdom.

Yuasa et al., Whisker Growth of L-menthol in coexistence with various excipents, International Journal of Pharmacutics 203, (2000), pp. 203-210, Tokyo, Japan.

Abdul et al., A Flexible Technology of Modified-Rlease Drugs: Multiple-Unite Pellet System (MUPS), J Controlled Release 147: 2-16 (2010).

Baranuskiene et al., Flavor Retention of Peppermint (*Mentha piperita* I.) Essential Oil Spray-Dried ni Modified Starches during Encapsulation and Storage, J. Agric. Food Chem., 2007, 55, 3027-3036.

Benes et al., Transmucosal, Oral Controlled-Release and Transdermal Drug Administration in Human Subjects: A Corssover Study with Melatonin, Journal of Pharmaceutical Sciences / 1115, vol. 86, No. 10, Oct. 1997.

Bogentoft et al., Influence of Food on the Absorption of Acetylsalicylic Acid From Enteric-Coated Dosage Forms, European J. Clin. Pharmacol., 14, 351-355, 1978.

Cellulose acetate phthalate enter coating (enerexusa.com/articles/enteric_coating.htm., last visit Feb. 6, 2014).

Chourasia et al., Pharmaceutical Approaches to Colon Targeted Drug Delivery Systems, J Pharm Pharmaceut Sci 6: 33-66 (2003).

Clark et al., Variations in Composition of Peppermint Oil in Relation to Production Areas, Economic Botany 35(1), 1981, pp. 59-69, Bronx, NY, USA.

Committee for Proprietary Medicinal Products, Note for Guidance On Quality of Modified Release Products: A: Oral Dosage Forms, B: Transdermal Dosage Forms, Jul. 29, 1999, The European Agency for the Evaluation of Medicinal Products, London.

Dey et al., Multiparticulate Drug Deliver Systems for Controlled Release, Tropical Journal of Pharmaceutical Research, Sep. 2008; 7(3): 1067-1075, Pharmacotherapy Group, Faculty of Pharmacy, University of Benin, Benin City, 300001 Nigeria.

Digenis, Geroge A., The in vivo behavior of multiparticulate versus single unit dose formulations, presented at Capsugel's Symposium in Seoul (Apr. 10, 1990) and Tokyo (Apr. 12, 1990).

Dong et al., Effect of processing parameters on the formation of spherical multinuclear microcapsules encapsulating peppermint oil by coacervation, Journal of Microencapsulation, Nov. 2007; 24(7): 634-646.

(56) References Cited

OTHER PUBLICATIONS

Faroongsarng et al., The Swelling & Water Uptake of Tablets III: Moisture Sorption Behavior of Tablet Disintegrants, Drug Development and Industrial Pharmacy, 20(5), 779-798, (1994).

Final Report on the Safety Assessment of *Mentha piperita* (Peppermint) Oil, *Mentha piperita* (Peppermint) Leaf Extract, *Mentha piperita* (Peppermint) Leaf, and *Mentha piperita* (Peppermint) Leaf Water, International Journal of Toxicology, 2001 20:61, online version at http;//ijt.sagepub.com/content/20/3/_suppl/61.

Galeotti et al., Menthol: a natural analgesic compound, Neuroscience Letters 322 (2002), pp. 145-148, Florence, Italy.

Grigoleit et al., Gastrointestinal clinical pharmacology of peppermint oil, Phytomedicine 12, (2005), pp. 607-611, Wiesbaden, Germany.

International Search Report of Jan. 29, 2014 for PCT/US2013/000217.

International Search Report dated Feb. 16, 2014 for PCT/US2013/061141.

International Search Report of Feb. 4, 2014 for PCT/US2013/061146.

ISR for PCT/US12/41226, dated Aug. 16, 2012.

Juergens, et al., The Anti-Inflammatory Activity of L-Menthol Compared to Mint Oil in Human Monocytes In Vitro: A Novel Perspective for Its Therapeutic Use in Inflammatory Diseases, Eur J. Med Res (1998) 3: 539-545, Dec. 16, 1998.

Kellow et al., Altered Small Bowel Motility in Irritable Bowel Syndrome is Corrected with Symptoms, Gastroenterology, 1987, vol. 92, pp. 1885-1893, Rochester, Minnesota, USA.

Kim et al. (The Influence of Surelease and Sodium Alginate on the In-Vitro Release of Tamsulosin Hydrochloride in Pellet Dosage Form., J Pharm Pharmacol, Jun. 2005; 57(6): 735-42.

Kline et al., Enteric-Coated pH-dependent peppermint oil capsules for the treatment of irritable bowel syndrome in children, J Pediatr 2001; 138: 125-8.

Lee et al, Design and evaluationof an oral controlled release delivery systme for melatonin in humans subjects, International Journal of Pharmaceutics 124 (1995) 119-127, College of Pharmacy, Kangwon National University, Chuncheon, South Korea, Department of Pharmaceutics, College of pHarmacy, Oregeon State University, Corvallis, OR 97331-3507, USA, Department of Psychiatry, School of Medicine, Oregon Health Sciences University, Portland, OR, USA.

Lee et al., Formulation and Release Characteristics of Hydroxypropyl Methycellulose Matrix Tablet Containing Melatonin, Drug Development and Industrial Pharmacy, 25(4), 493-501 (1999), Biological Rhythm and Controlled Release Laboratory, College of Pharmacy, Kangwon National University, Chuncheon 200-709, Korea.

Liu et al., pH-resonsive amphiphilic hydrogel networks with IPN structure; A strategy for controlled drug release, International Journal of Pharmaceutics 308 (2006) 205-209, Department of Applied Chemistry, School of Science, Northwestern Polytechnic University, Xi'an 710072, PR China.

Macpherson et al., More than cool: promiscuous relationships of menthol and other sensory compounds, Mol. Cell. Neurosci, vol. 32, 2006, pp. 335-343.

Mcintyre et al., Melatonin Rhythm in Human Plasma and Saliva, Journal of Pineal Research 4:177-183 (1987), Psychoendocrine Research Unit, Department of Psychiatry, Austin Hospital Heidelbert (I.M.M., T.R.N., G.D.B.), and Department of Psychology, Brain Behaviour Research Institute, Latrobe University, Bundoora (S.M. A.), Victoria, Australia.

Menthols (inchem.org/documents/sids/sids/MENTHOLS.pdf, last visit Feb. 6, 2014).

Micklefield, et al., Effects of Peppermint Oil and Caraway Oil on Gastroduodenal Motility, Phytother. Res. 14, 20-23 (2000).

Office Action for U.S. Appl. No. 14/033,713 dated May 14, 2014.

Office Action for U.S. Appl. No. 14/033,737 dated Apr. 23, 2014.

Office Action for U.S. Appl. No. 14/064,685 dated Sep. 24, 2014.

Office Action for U.S. Appl. No. 14/064,685 dated Mar. 7, 2014.

Office Action for U.S. Appl. No. 14/524,326, dated Apr. 23, 2015.

Pilbrant et al., Development of an oral formulation of omeprazole, Scand J. Gastroenterol, 1985, vol. 20 (suppl. 108, pp. 113-120, Molndal, Sweden.

Pittler et al., Peppermint Oil for Irritable Syndrome: A Critical Review and Metaanalysis, The American Journal of Gastroenterology, vol. 93, No. 7, 1998, 1131-1135.

Rees et al., Treating Irritable Bowel Syndrome with Peppermint Oil, British Medical Journal, Oct. 6, 1979.

Rohloff et al., Effect of Harvest Time and Drying Method of Biomass Production, Essential Oil Yield, and Quality of Peppermint (*Mentha* x *piperita* L.), J. Agric. Food Chem., 2005, vol. 53, pp. 4143-4148 Hedmark, Norway.

RXMED: Pharmaceutical Information—Colpermin, Peppermint Oil Symptomatic Relief of Irritable Bowel Syndrome, Jan. 4, 2010.

Sibanda et al., Experimental Design for the Formulation and Optimization of Novel Cross-Linked Oilispheres Developed for In Vitro Site-Specific Release of Mentha piperita Oil, AAPS PharmSciTech 2004; 5(1) Article 18 (http://www.aapsharmscitech.org, submitted Nov. 5, 2003, Accepted Feb. 18, 2004.

Somerville et al., Delayed release peppermint oil capsules (Colpermin) for the spastic colon syndrome: a pharmacokinetic study, Br. J. clin. Pharmac., (1984), vol. 18, pp. 638-640, Ipswich, United Kingdom.

Stevens et al., The short term natural history of irritable bowel syndrome: a time series analysis, Behav. Res. Ther., vol. 35, No. 4, pp. 319-326, 1997, Albany, NY, USA.

Thompson, Shaun, List of Proton Pump Inhibitors, Mar. 12, 2011, http://www.livestrong.com/article/26705-list- proton-pump-inhibitors.

Furmanowa et al.; XI *Carum carvi* L. (Caraway); "In Vitro Culture Embryogenesis and the Production of Aromatic Compounds"; Springer; vol. 15; pp. 176-177; 1991.

Yu Songhua et al.; "Investigation on Preparation and Stability of Gelatin Coated Garlic Oil Pellets"; The Chinese and Foreign Health Abstract, No. 25, vol. 7, pp. 88-89; Nov. 23, 2010.

\* cited by examiner

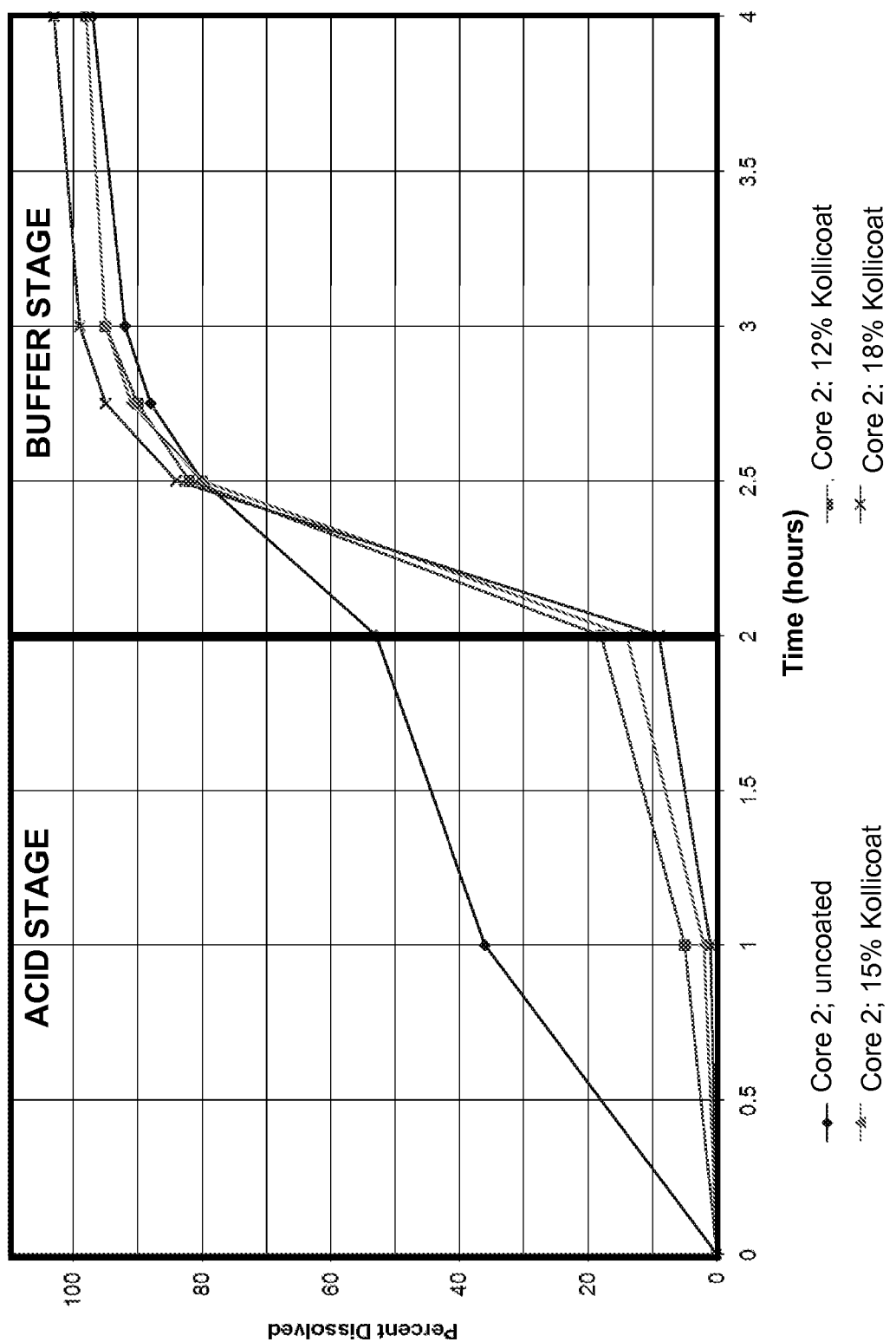

MULTIPARTICULATE L-MENTHOL FORMULATIONS AND RELATED METHODS

CROSS-REFERENCE TO RELATED APPLICATIONS

This is a continuation of application Ser. No. 14/064,685, filed Oct. 28, 2013 which is a continuation of application Ser. No. 13/367,747, filed Feb. 7, 2012, now U.S. Pat. No. 8,568,776, which claims priority to App. No. 61/441,716 filed Feb. 11, 2011 entitled "Multiparticulate Formulations and Related Methods," and App. No. 61/486,523, filed May 16, 2011 entitled "Multiparticulate Formulations and Related Methods." Each of these prior applications is incorporated by reference herein in its entirety.

FIELD

This relates to multiparticulate formulations for delivering high purity L-menthol to the intestines, and, more particularly, to enteric coated high purity L-menthol multiparticulate formulations and related methods.

BACKGROUND

Essential oils have been used for their bioactivity for quite some time. Some essential oils are currently being used as medicaments. For example the plants *Mentha piperita* or *Mentha arvensis*, are the two primary sources of peppermint oil. Peppermint oil is effective at treating the symptoms of gastrointestinal disorders such as irritable bowel syndrome (IBS). These symptoms can include pain, discomfort, bloating, constipation, and/or diarrhea. Clinical trials have demonstrated significant alleviation of the symptoms associated with IBS through the use of peppermint oil in single unit capsules coated with the cellulose acetate-phthalate enteric polymer or other enteric-coating polymers.

For maximal efficacy in the treatment of IBS and to avoid related complications, peppermint oil should be locally delivered to the intestines, while avoiding the stomach. If peppermint oil is released from its dosage form prior to passing through the pyloric sphincter into the intestines, it can irritate the mucous membranes in the digestive tract. Releasing peppermint oil directly into the stomach can cause heartburn (gastric irritation) and gastro-esophageal reflux disease. Therefore, since peppermint oil is usually administered orally, it should preferably be prepared with an enteric coating.

Enteric-coated single unit capsules for treating irritable bowel syndrome that contain peppermint oil currently exist. But, even though the enteric coated single unit capsules are meant to delay the release of peppermint oil until after the capsule enters the intestines, this approach to treating IBS has several drawbacks. The drawbacks include premature release of the peppermint oil from the capsule in the stomach, resulting in heartburn. Also, the accidental chewing of the capsule causes the enteric coat to rupture prematurely and release the oil in the stomach. Using current formulations of peppermint oil, significant doses are required to achieve an efficacious concentration of peppermint oil in the body. For example, each of the above referenced capsules contains about 200 mg of peppermint oil and must be taken three times a day, 30-60 minutes prior to a meal. The dose can be increased to two capsules taken three times daily in some situations.

Enteric-coated peppermint oil is typically administered as a single-unit formulation. However, in a single-unit formulation, the amount of peppermint oil absorbed by the intestines can vary from dose to dose for several reasons. First, single-unit enteric capsule formulation can get attached to the esophagus because of the muco-adhesive properties of the enteric coat and therefore not enter the stomach within the desired time frame. The single unit enteric coated capsules, like enteric coated single unit tablets have been shown to not release the active ingredient from the single unit formulation because the single unit's size is too large to pass through the constriction in the stomach's pylorus valve. The enteric coat of the capsule may also prematurely crack or rupture because of the force created by the swelling of the gelatin (or hypromellose) seal coat against the thinner outer enteric coat. Peppermint oil containing capsules have a lower specific gravity than the stomach contents, and tend to float rather than settle and then pass through the pylorus constriction between the stomach and the lower intestines.

Non-disintegrating tablets or capsules given with food may stay in the stomach for long times, 10 to 15 hours, before they are emptied into the small intestine. Small particles, with diameters less than 3 mm, are emptied from the stomach more regularly, regardless of whether they are given with food. The 10 to 15 hours that an enteric coated hard gelatin or hypromellose capsule can get exposure to gastric conditions in a fed state may cause the enteric coat to rupture and the hard gelatin (or hypromellose) seal coat to dissolve, resulting in the peppermint oil being released in the stomach and causing heartburn or gastric irritation.

Even when the single unit enteric coated capsule passes through the pylorus intact in a timely fashion, when it reaches the small intestine the coating dissolves and a bolus of oil is released in the intestine. This dosage dumping, a situation in which the active ingredient is released and gives very high local exposure in a segment of the intestine, is also undesirable because it prevents uniform and steady exposure of peppermint oil in the G.I. lumen. This high local exposure to one section of the G.I. lumen may actually aggravate symptoms of IBS.

Single-unit formulations are also significantly influenced by the quantity of food in the stomach. Gastric emptying rates of single unit doses are erratic and unpredictable. Single-unit enteric-coated tablets or capsules taken with food may stay in the stomach for many hours before being emptied into the small intestine. As a result, single-unit formulations present both inter and intra-subject variability with respect to the bioavailable concentration of active ingredient. According to regulatory guidelines, enteric-coated single-unit capsules can never be bioequivalent with multiple-unit enteric-coated dosage forms. A single-unit enteric preparation containing peppermint oil was disclosed in U.S. Pat. No. 4,687,667, which is hereby incorporated by reference in its entirety except to the extent it may be inconsistent with this application.

The currently available delayed release single unit dosage forms containing enteric-coated peppermint oil have another limitation. They dump their primary active ingredient, L-menthol, when the enteric layer disintegrates. The terminal half-life of L-menthol is ~1.34 hours. Therefore, the systemic exposure of L-menthol is limited to approximately 4 hours, resulting in the need for frequent dosing (usually three times a day) to relieve the symptoms of IBS. The use of a single unit non-disintegrating delayed release dosage form is undesirable due to unpredictable absorption and longer residence time in the stomach.

SUMMARY

An L-menthol pharmaceutical dosage form includes an effective amount of L-menthol for treating a gastrointestinal disorder. The L-menthol is within a plurality of particulates. The particulates have a core and an enteric coating over the core. The core includes an L-menthol source that is at least 80% pure L-menthol. The enteric coating is effective to substantially prevent release of the L-menthol from the core into a gastric pH environment and to release L-menthol from the core into an intestinal pH environment.

A method of treating a gastrointestinal disorder includes administering an effective amount of an L-menthol-containing dosage form for treating a gastrointestinal disorder to a subject having a gastrointestinal disorder. The L-menthol is within a plurality of particulates. The particulates have a core and an enteric coating over the core. The core includes an L-menthol source that is at least 80% pure L-menthol. The enteric coating is effective to substantially prevent release of the L-menthol from the core into a gastric pH environment and to release L-menthol from the core into an intestinal pH environment.

The effective amount of L-menthol may be about 10 mg to about 200 mg.

The L-menthol source may be crystalline L-menthol or micronized crystalline L-menthol.

The enteric coating may include a methacrylic acid based copolymer.

The plurality of particulates may be contained in a capsule or packet-type dosage form for oral administration.

The core may include about 30% w/w to about 70% w/w L-menthol, about 25% w/w to about 60% w/w microcrystalline cellulose, and about 0.5% w/w to about 4% w/w hypromellose.

These and other objects, aspects, and advantages of the present invention will be better appreciated in view of the drawings and following description of certain embodiments.

BRIEF DESCRIPTION OF THE DRAWINGS

FIG. 1 is a graph of the dissolution of various samples of multiparticulate formulations of the invention in a 0.1 HCl solution (acid stage) and subsequently a pH=6.8 buffer (buffer stage).

DETAILED DESCRIPTION OF EMBODIMENTS

In the Summary above and in the Detailed Description of Embodiments and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the invention will be described more fully with reference to the accompanying drawing. This invention may, however, be embodied in many different forms and should not be construed as limited to the embodiments set forth herein. Rather, these embodiments are provided so that this disclosure will convey preferred embodiments of the invention to those skilled in the art.

The efficacy of peppermint oil in controlling smooth muscle contraction can be substituted by its main bio-active constituent, L-menthol. Peppermint oil derived from *Mentha piperita* only contains up to 50% menthol and *Mentha arvensis* contains only approximately 70-80% menthol. The other components of peppermint oil include menthone, pulegone, menthofuran, and limone, which may cause undesirable side effects or diminish the effectiveness of the L-menthol. In contrast to peppermint oil, which is primarily available as a liquid, L-menthol is available in a liquid and crystalline powder form. The inventors have advantageously developed a unique combination of ingredients and processing methods for providing an enteric coated multiparticulate formulation comprising high purity liquid or solid L-menthol.

One aspect of the invention is to provide a multiparticulate formulation comprising solid L-menthol for treating gastrointestinal disorders such as gastrointestinal discomfort and irritable bowel syndrome. This is advantageous over typical peppermint oil formulations because the undesirable menthone, pulegone, menthofuran, and limone are not co-administered with L-menthol to a patient who takes the formulation, thus preventing the undesirable side effects or reduced efficacy of L-menthol that may result.

Further, because it is desirable for L-menthol to be released into the intestines as opposed to the stomach, the formulation provides a reduced release in the stomach and an elevated release at a substantially neutral pH, such as the pH found in the intestines. In a preferred embodiment, the formulation allows for release of at least about 80% of the L-menthol within about two hours of being placed in a substantially neutral pH environment. As used herein, a substantially neutral pH environment means an environment having a pH of about 7, including, but not limited to a pH of between about 6.5 to about 7.5, also including the pH environment of the intestines. In another preferred embodiment, the formulation allows for the release of no more than about 10% of the L-menthol within about 2 hours of being placed in a 0.1 N HCl solution and, subsequently, no less than about 85% of the L-menthol within about 45 minutes of being placed in a substantially neutral pH environment, which is consistent with USP 711 enteric protection specifications.

The solid L-menthol multiparticulate formulations of the invention provides an advantageous L-menthol oral delivery vehicle that can be administered to a patient. A multiparticulate formulation of the invention comprise a plurality of individual particulates that are preferably spheroidal in shape and are preferably configured for incorporation into a capsule or packet-type oral delivery dosage form.

The invention also provides a unique method of making the multiparticulate formulations in which the temperature of the formation process is controlled and the enteric coating material chosen to prevent L-menthol from significantly volatilizing or degrading, thereby allowing the formulation of the invention to comprise L-menthol supplied from a high purity L-menthol source such as a purified liquid L-menthol or solid L-menthol preferably at or above 80% purity.

The data provided in the examples section show that the inventors have successfully produced a high purity enteric coated multiparticulate L-menthol composition with a dissolution profile consistent with USP 711 specifications. This formulation allows for prolonged duration of action, more reliable dosing, and reduced drawbacks from the undesirable L-menthol derivatives or degradants when compared to current marketed peppermint oil formulations.

The multiparticulates of the invention comprise a plurality of particulates which are preferably spheroidal in shape. Each particulate is sized to fit through the pyloric sphincter in a relaxed state. The diameter of the particulates is preferably in the range of about 0.1-3 mm, more preferably about 1-2.5 mm.

The particulates are comprised of a preferably spheroidal core with an enteric coating over the core. The particulates may also have an optional sub-coating between the core and enteric coating. In a preferred embodiment, the sub-coating comprises hydroxypropyl methyl cellulose, also known as "HPMC" or "hypromellose." The particulates may also include one or more additional coatings such as a sealant coating or a color coating on the enteric coating. In a preferred embodiment, the sub-coating is hypromellose E5. The sub-coating is preferably between about 1-5% w/w of the enteric coated particulate.

The core comprises the primary active ingredient, which is high purity L-menthol such as solid L-menthol. Solid L-menthol is a crystalline material at room temperature, has a melting point at standard pressure of about 42°-45° C., and may undergo sublimation at slightly above room temperature. The core may also comprise an antioxidant, which can maintain the purity of the L-menthol to prevent the L-menthol from oxidizing into undesirable derivatives. Examples of antioxidants include, but are not limited to tocopherol (vitamin E,) BHT (butylated hydroxy toluene), BHA (butylated hydroxy anisole), and ascorbic acid. The core may also comprise one or more inactive ingredients.

The term "solid L-menthol" means L-menthol in its solid form, preferably in its crystalline form. In the crystalline form, L-menthol is substantially free of undesirable impurities. Although it may not always be necessary, it is preferred that the starting material for L-menthol appear as visually perceptible L-menthol crystals that are then ground into a polycrystalline powder. During development of the formulation of the invention, the inventors found that micronizing the L-menthol produced good results. Although not intending to be bound by theory, it is believed that micronizing the L-menthol produces more L-menthol surface area, which improves L-menthol's aqueous solubility. It is preferred, however, that the L-menthol be micronized without raising the temperature of the L-menthol enough to degrade the L-menthol molecules, cause L-menthol to melt, or cause L-menthol to undergo sublimation. A suitable technique for producing micronized L-menthol crystals involves jet milling. A preferred concentration of L-menthol in the core is between about 30% to 70% w/w of the total enteric coated particulate.

The core may also include one or more of filler, stabilizer, binder, surfactant, processing aid, or disintegrant. By way of example only, suitable materials for performing these functions are provided. A suitable filler includes a pharmaceutically suitable filler. In one embodiment, the filler is microcrystalline cellulose. A suitable binder includes a pharmaceutically suitable binder. In a preferred embodiment, the binder is a cellulosic water soluble polymer such as cellulose ether. Because L-menthol is not highly soluble in water, it may be advantageous to include a surfactant as a solubilizing agent. A preferred solubilizing agent is polysorbate 80 or sodium lauryl sulfate ("SLS"). It was discovered that the solubilizing agent improved the wettability and, therefore, the rate and extent of release of L-menthol from the particulates. Polysorbate 80 also enhances absorption of L-menthol into the plasma.

A suitable processing aid includes a pharmaceutically suitable processing aid such as for improving the flowability of the core materials during processing. In a preferred embodiment, the processing aid is colloidal silicon dioxide.

A suitable disintegrant includes a pharmaceutically suitable disintegrant. In a preferred embodiment, the disintegrant is croscarmellose sodium.

A preferred composition for the core comprises about: 30-70% w/w micronized L-menthol; about 2% to 15% w/w processing aid; about 25 to 60% w/w filler; about 4% to 6% w/w disintegrant; about 0.5% to 4% w/w binder; about 1% to 3% w/w solubilizing agent; and about 0.5% to 4% w/w antioxidant. Here the % w/w is relative to the total weight of the enteric coated particulate.

A listing of ingredients for two exemplary embodiments of the core is shown in Table 1. In Table 1, the % w/w is based on the uncoated core. For Core 1, L-Menthol was supplied as 95% w/w L-Menthol/5% w/w CAB-O-SIL M5P (Silicon Dioxide) and was milled using Fitz Mill equipment. For Core 2, L-Menthol was supplied as 95% w/w L-Menthol/5% w/w CAB-O-SIL M5P (Silicon Dioxide) and was milled using Jet Pulverizer equipment. The % represents the theoretical quantity of L-Menthol in the blend. Core 1 used AVICEL PH-101 as the filler and Core 2 used AVICEL PH-102 as the filler. These are chemically identical microcrystalline cellulose and vary only by particle size.

The enteric coating is applied over the uncoated core or, if the sub-coating is present, over the sub-coating. The enteric coating is preferably applied so that it comprises about 5-35% w/w of the enteric coated particulate. A preferred enteric coating material is a methacrylic acid based material such as a methacrylic acid based co-polymer. Examples of suitable methacrylic acid based copolymers include EUDRAGIT L30D-55 (poly(meth)acrylate-based coating) or KOLLICOAT MAE 30 DP. KOLLICOAT® MAE 30 DP is a methacrylic acid-ethyl acrylate co-polymer. These materials may be combined with other materials such as plasticizers for forming an enteric coating solution. In a typical embodiment, an enteric coating solution comprises about 20-40% w/w water, about 0.5-1.5% w/w plasticizer, about 5-15% anti-adherent, and about 40-70% copolymer. By way of example only, a suitable plasticizer is triethyl citrate and a suitable anti-adherent is PLASACRYL T20. PLASACRYL T20 is an emulsion of anti-tacking agent and plasticizer and contains water, glyceryl monostearate, triethyl citrate and polysorbate 80.

Although it may not always be necessary, it is preferred that the enteric coating material be applied to the core without heating the core above about 30° C. This can be particularly difficult considering that enteric coatings are typically applied in a fluidized bed coater at sufficient air inlet temperature to result in a product temperature of about 38-42° C. Unfortunately, at such a high temperature, L-menthol tends to degrade and volatilize. This made it very difficult to produce a high purity, solid L-menthol formulation that met or approximated the desired USP 711 enteric specifications. The inventors found that both EUDRAGIT L30D-55 and KOLLICOAT MAE 30 DP were suitable because they could be reliably applied to the cores at lower temperatures with good coalescence between the enteric coating and the underlying material. Without intending to be bound by theory, this may be because the glass transition temperature $T_g$ of these methacrylic acid based copolymers is roughly about 26° C. and depends on the plasticizer used. These methacrylic acid copolymer based enteric coating materials do not require pH sensitive pore formers to dissolve at or near neutral pH.

A listing of the ingredients in an exemplary embodiment of enteric coated particulates is provided in Table 2. The core in this example is Core 2. The % w/w is based on the weight enteric coated particulate.

Methods of making the multiparticulate formulations in accordance with another aspect of the invention will now be described. The core is typically prepared by wet granulating the core materials into a wet mass, extruding the wet mass to form an extrudate, cutting the extrudate into a plurality of core pieces, and spheronizing the core pieces. If the antioxidant is in a liquid solution, the liquid antioxidant solution may be sprayed into the wet mass. The spheronized core pieces are preferably dried to <3% based on the Karl Fischer method. The spheronized core pieces are then coated with the enteric coating material. The enteric coating is typically applied in a fluidized bed coater. The enteric coated particulates are subsequently dried, to <3% (Karl Fischer). The dried enteric coated multiparticulates may then be prepared into a suitable pharmaceutical dosage form such as a capsule or tablet, for example. A typical preferred capsule contains about 250 mg of the particulates. Depending on the desired dosage, however, this may be adjusted.

The inventors found that L-menthol may sublimate, oxidize, or otherwise degrade during processing if the processing parameters are not carefully controlled. For example, the mechanical force of granulating the L-menthol may cause it to heat, thereby resulting in sublimation, oxidation, and/or degradation. However, using a technique for granulating the L-menthol, such as jet milling, allowed for the inventors to produce cores in which the integrity and amount of raw L-menthol was retained. Aside from issues related to granulation, drying the core pieces and applying the enteric coating can adversely heat the L-menthol as well. It is preferred that throughout the process, the temperature of the formulation be maintained at or below 30° C. and, more preferably, at or below 25° C.

The multiparticulate formulations of the invention are preferably formulated to be taken orally by a human or animal patient and to ensure that the patient receives an effective amount of high purity L-menthol over the course of several hours after ingestion. An effective amount is an amount that is sufficient to affect a disease or process in the body. In a preferred embodiment a dose of a multiparticulate formulation provides about 10 mg to 200 mg or, more preferably, about 90-110 mg of L-menthol. Doses of the multiparticulate formulation may be administered sporadically when needed for treating acute inflammations of the G.I. tract or may be administered as part of a long term regimen for treating irritable bowel syndrome. A patient may be a human or animal patient.

Accordingly, another aspect of the invention is to provide a method of treating a gastrointestinal disorder, the method comprising administering a multiparticulate formulation of the invention to the patient (human or animal).

EXAMPLES

This section describes examples of certain preferred embodiments of the invention. The examples are not intended to limit the scope of the invention in any way.

Example 1: Preparation of Multiparticulate Formulations

Experimental Details. The equipment utilized to create the formulations herein includes the following: top loading balances, hand screens (12, 14, 16, 18, Pan, 70 mesh), Rotap sieve shaker, IKA mixer, KitchenAid food processor (pre-milling), Fitz mill equipped with a 0.065" screen, Jet Mill, Key International high sheer mixer, Glatt GPCC-3 fluid bed drier, Glatt GPCC-3 fluid bed dried with 7" Wurster, Karl Fischer moisture analyzer, and a spheronizer.

Preparation of Core 1. Core 1, shown in Table 1, was prepared as described above utilizing the following settings. The wet granulation settings were: impeller speed 300 rpm, chopper speed 3450 rpm, wet massing time 80-90 seconds, maximum Impeller Power 5.5-6.2 amps. The extrusion settings were: impeller speed 25 rpm, feeder speed 30 rpm, screen size 1.2 mm. Extrudates were charged to a spheronizer rotating at 500 rpm. Core 1 particulates were dried at 17-23° C. at 45 cfm air flow for 60-75 minutes.

Preparation of Core 2. Core 2, shown in Table 1, was prepared as described above utilizing the following settings: The wet granulation setting were: impeller speed 640 rpm, chopper speed 9450 rpm, maximum impeller power 6-7 amps. The extrusion settings were: impeller speed 25 rpm, feeder speed 30 rpm, screen size 1.2 mm. Extrudates were charged to a spheronizer rotating at 900-925 rpm. Core 2 particulates were dried at 17-23° C. at 45 cfm air flow for 60-75 minutes.

Application of sub-coating. Core 1 and Core 2 particulates were separated based on their size. The fraction that fell within the 14-18 mesh size was chosen for sub-coating. The cores were placed into a fluidized bed dryer and the sub-coating was sprayed onto the cores in the form of a 10% hypromellose (hypromellose E5) aqueous solution that was at room temperature.

Preparation of enteric coating solutions. Two of the enteric coatings that were evaluated individually comprised EUDRAGIT L30D-55 and KOLLICOAT MAE 30 DP. The enteric coatings were applied to the cores in a fluidized bed coater (7" wurster) as a liquid solution. Tables 3 and 4 show the ingredients used in the EUDRAGIT coating (enteric coating solution A) and the KOLLICOAT coating (enteric coating solution B), respectively.

Enteric coating solution A was applied to the cores using the following parameters: the inlet temperature was maintained between 22.7° C. and 23° C.; the exhaust temperature was maintained between 27° C. and 30° C.; the air flow was maintained between 20 and 22 cfm; the spray rate was maintained between 4.15 and 4.4 g/min; the product temperature was maintained between 19° C. and 22° C.

Enteric coating solution B was applied to the cores using the following parameters: the inlet temperature was maintained between 22.7° C. and 23° C.; the exhaust temperature was maintained between 28° C. and 30° C.; the air flow was maintained between 20 and 22 cfm; the spray rate was maintained at about 4.25 g/min; and the product temperature was maintained between 19° C. and 22° C.

Example 2: Evaluation of Prepared Multiparticulate Formulations

The prepared multiparticulate formulations were evaluated to determine whether they met or approximated the desired USP 711 enteric specifications. To meet USP 711 enteric specifications, less than 10% of the active ingredient should be released in 2 hours in a 0.1 N HCl solution ("acid stage"). Subsequently, no less than 85% of the active ingredient should be released in 45 minutes in a pH 6.8 buffer ("buffer stage").

The data in Tables 5 and 6 confirm that both the EUDRAGIT and KOLLICOAT coatings can successfully be used with crystalline L-menthol to form enteric coated L-menthol multiparticulate formulations that meet or approximate USP 711 enteric specifications. In Tables 5 and 6, the batch identification refers to the core used, the coating on the core, and the preparation number for the specific formulation. A 3% w/w hypromellose sub-coating was applied to all of the cores before they were coated with the specified enteric coating.

In the acid stage, the samples were placed into a 0.1 N HCl solution for two hours. The samples were subsequently removed from the acid stage and placed in the buffer stage for the number of hours specified. The numbers indicate the % L-menthol released at the specified number of hours.

FIG. 1 is a graph of the dissolution profile for several of the multiparticulate formulations comprising cores coated with KOLLICOAT. The % w/w of KOLLICOAT relative to the weight of the particulate was varied to determine which % provides the most preferred results. FIG. 1 very clearly shows that the dissolution profile of the enteric coated particulates is much improved relative to the uncoated cores. The data for the enteric coated multiparticulates is approximately sigmoidal in shape with a slow increase within the first two hours in the acid stage and abrupt increase after two hours once the buffer stage begins. When the KOLLICOAT enteric coating is about 18% w/w of the of the weight of the particulate, less than 10 of the L-menthol is released in the acid stage and nearly 100% of the L-menthol is released within 2 hours in the buffer stage.

The invention has been described above with reference to the accompanying drawings and preferred embodiments. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

Any publications, patent applications, patents, and other references mentioned herein are incorporated by reference in their entirety as if they were part of this specification. However, in case of conflict, the present specification, including any definitions, will control.

In the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

TABLE 1

Ingredients of two exemplary embodiments of the core.

| Ingredient | Core 1 (grams/% w/w) | Core 2 (grams/% w/w) | Ingredient Function |
|---|---|---|---|
| L-Menthol | 249.6/49.92 | 241.92/48.38 | Active ingredient |
| CAB-O-SIL M5P (Colloidal Silicon Dioxide) | 10.4/2.08 | 26.88/5.38 | Processing Aid |
| AVICEL (Micro Crystalline cellulose) | 190.00/38.00 | 176.20/35.24 | Filler |
| AC-DI-SOL (Croscarmellose Sodium) | 30.00/6.00 | 30.00/6.00 | Disintegrant |
| Hypromellose (METHOCEL A15 Premium) | 10.00/1.00 | 10.00/1.00 | Binder |
| Polysorbate 80 | 5.00/2.00 | 10.00/2.00 | Solubilizing Agent |
| Ascorbic Acid | 5.00/1.00 | 5.00/1.00 | Antioxidant |
| Water (% of dry mass) | (93.00%) | (86.16%) | |

TABLE 2

Ingredients of an exemplary embodiment of enteric-coated particulates.

| Ingredient | Ingredient % w/w in Finished EC Multiparticulate | Ingredient Weight in Finished Dosage Form (mg) | Ingredient Function |
|---|---|---|---|
| L-Menthol | 43.816 | 100.000 | Active ingredient |
| Cab-O-Sil M5P (Colloidal Silicon Dioxide) | 2.804 | 6.399 | Processing aid |
| AVICEL pH102 | 30.234 | 69.001 | Filler |
| AC-DI-SOL (FMC; Croscarmellose Sodium) | 5.148 | 11.748 | Disintegrant |
| METHOCEL A15 Premium | 1.716 | 3.916 | Binder |
| Polysorbate 80 | 0.858 | 1.958 | Solubilizing agent |
| Ascorbic Acid | 0.858 | 1.958 | Antioxidant |
| Hypromellose E5 | 2.627 | 5.995 | Sub-coating |
| KOLLICOAT MAE 30 DP Solids | 10.369 | 23.666 | Source of methacrylic copolymer |
| Triethyl Citrate | 0.538 | 1.227 | Plasticizer |
| PLASACRYL T20 | 1.033 | 2.358 | Anti-Adherent |
| Water[1] | | | |

[1]Evaporates

TABLE 3

Enteric Coating Solution A: EUDRAGIT L30D-55 (Evonik)

| Ingredient | grams |
|---|---|
| EUDRAGIT L30D-55 (30% w/w solids) | 578.7 |
| Triethyl Citrate | 9 |
| PLASACRYL T20 | 86.5 |
| Water* | 325.8 |

*Evaporates

TABLE 4

Enteric Coating Solution B: KOLLICOAT MAE 30 DP (BASF)

| Ingredient | grams |
|---|---|
| KOLLICOAT 30 DP 55 (30% w/w solids) | 578.7 |
| Triethyl Citrate | 9 |

TABLE 4-continued

Enteric Coating Solution B: KOLLICOAT MAE 30 DP (BASF)

| Ingredient | grams |
|---|---|
| PlasACRYL T20 | 86.5 |
| Water* | 325.8 |

*Evaporates

TABLE 5

Dissolution Results for various EUDRAGIT coated and uncoated multiparticulate formulations.

| | % Dissolved per Hour | | | | | | | | | |
|---|---|---|---|---|---|---|---|---|---|---|
| | Acid Stage 0.1N HCl | | | Buffer Stage pH = 6.8 buffer Time (hr) | | | | | | |
| Batch Identification | 1 | 2 | 2.25 | 2.5 | 2.75 | 3 | 4 | 6 | 8 | 10 |
| Uncoated Core 1; Preparation 1 | 49 | 52 | 149 | 105 | 101 | 99 | 97 | 95 | 94 | 92 |
| Uncoated Core 1; Preparation 2 | 34 | 41 | 72 | 77 | 77 | 76 | 75 | 75 | 75 | 74 |
| Core 1; Evonik EUDRAGIT L30D (12% w/w) + 0.5% SLS | 2 | 5 | 35 | 65 | 77 | 80 | 86 | 85 | 85 | 84 |
| Core 1; Evonik EUDRAGIT L30D (12% w/w) + 1.0% SLS | 2 | 5 | 42 | 73 | 83 | 88 | 91 | 90 | 90 | 89 |

TABLE 6

Dissolution Results for various KOLLICOAT coated and uncoated multiparticulate formulations.

| | % Dissolved per Hour | | | | | | |
|---|---|---|---|---|---|---|---|
| | Acid Stage 0.1N HCl | | Buffer Stage pH = 6.8 buffer Time (hr) | | | | |
| Batch Identification | 1 | 2 | 2.25 | 2.5 | 2.75 | 3 | 4 |
| Uncoated Core 2; Preparation 1 | 32 | 46 | | 80 | 89 | 93 | 96 |
| Uncoated Core 2; Preparation 2 | 33 | 47 | | 76 | 86 | 91 | 95 |
| Uncoated Core 2; Preparation 3 | 31 | 46 | | 75 | 86 | 91 | 95 |
| Core 2; KOLLICOAT MAE 30 DP (12% w/w); Preparation 1 | 5 | 16 | | 72 | 82 | 86 | 93 |
| Core 2; KOLLICOAT MAE 30 DP (12% w/w); Preparation 2 | 5 | 15 | | 73 | 82 | 86 | 92 |
| Core 2; KOLLICOAT MAE 30 DP (12% w/w); Preparation 3 | 5 | 15 | | 75 | 82 | 86 | 91 |
| Uncoated Core 2; Preparation 4 | 36 | 53 | | 80 | 88 | 92 | 97 |
| Core 2; KOLLICOAT MAE 30 DP (12% w/w); Preparation 4 | 5 | 18 | | 82 | 90 | 95 | 98 |
| Core 2; KOLLICOAT MAE 30 DP (15% w/w); Preparation 1 | 2 | 14 | | 80 | 91 | 95 | 98 |
| Core 2; KOLLICOAT MAE 30 DP (18% w/w); Preparation 1 | 1 | 9 | | 84 | 95 | 99 | 103 |

That which is claimed is:

1. An L-menthol pharmaceutical dosage form comprising an effective amount of L-menthol for treating a gastrointestinal disorder, the L-menthol being within a plurality of particulates having:
   (a) a spheronized extrudate core including solid crystalline L-menthol intermixed with a pharmaceutically acceptable binder and a pharmaceutically acceptable filler; and
   (b) an enteric coating over the core, the enteric coating being effective to substantially prevent release of the L-menthol from the core into a gastric pH environment and to release L-menthol from the core into an intestinal pH environment;
   wherein the effective amount of L-menthol is about 10 mg to about 200 mg;
   wherein the plurality of particulates are combined in a capsule or packet-type dosage form for oral delivery.

2. The L-menthol pharmaceutical dosage form of claim 1, wherein the solid crystalline L-menthol is micronized crystalline L-menthol.

3. The L-menthol pharmaceutical dosage form of claim 1, wherein the enteric coating includes a methacrylic acid based copolymer.

4. The L-menthol pharmaceutical dosage form of claim 1, wherein the particulates are spheroidal and have a diameter of 0.1 mm to 3 mm.

5. The L-menthol pharmaceutical dosage form of claim 1, wherein:
   the particulates are spheroidal and have a diameter of 0.1 mm to 3 mm;
   the solid crystalline L-menthol is micronized crystalline L-menthol; and
   the enteric coating includes a methacrylic acid based copolymer.

6. The L-menthol pharmaceutical dosage form of claim 1, wherein the core includes about 30% w/w to about 70% w/w L-menthol, about 25% w/w to about 60% w/w microcrystalline cellulose as the pharmaceutically acceptable filler, and about 0.5% w/w to about 4% w/w hypromellose as the pharmaceutically acceptable binder.

7. A method of treating a gastrointestinal disorder, the method comprising:
   administering the L-menthol pharmaceutical dosage form of claim 1 in an effective amount for treating a gastrointestinal disorder to a subject having a gastrointestinal disorder.

8. The method of claim 7, wherein the gastrointestinal disorder is irritable bowel syndrome.

9. The method of claim 7, wherein the gastrointestinal disorder causes inflammation of the subject's gastrointestinal tract.

10. The method of claim 7, wherein the solid crystalline L-menthol is micronized crystalline L-menthol.

11. The method of claim 8, wherein the enteric coating includes a methacrylic acid based copolymer.

12. The method of claim 7, wherein the particulates are spheroidal and have a diameter of 0.1 mm to 3 mm.

13. The method of claim 7, wherein:
the particulates are spheroidal and have a diameter of 0.1 mm to 3 mm;
the solid crystalline L-menthol is micronized crystalline L-menthol; and
the enteric coating includes a methacrylic acid based copolymer.

14. The method of claim 7, wherein the core includes about 30% w/w to about 70% w/w L-menthol, about 25% w/w to about 60% w/w microcrystalline cellulose, and about 0.5% w/w to about 4% w/w hypromellose.

15. The L-menthol pharmaceutical dosage form of claim 1, wherein the spheronized extrudate core is spheroidal.

16. The L-menthol pharmaceutical dosage form of claim 1, wherein the solid crystalline L-menthol, pharmaceutically acceptable binder, and pharmaceutically acceptable filler are within the extrudate of the spheronized extrudate core.

* * * * *